United States Patent
Yagi et al.

(10) Patent No.: US 10,558,116 B2
(45) Date of Patent: Feb. 11, 2020

(54) METHOD FOR PREPARING SYNTHETIC QUARTZ GLASS SUBSTRATE

(71) Applicant: SHIN-ETSU CHEMICAL CO., LTD., Tokyo (JP)

(72) Inventors: Hisashi Yagi, Joetsu (JP); Daijitsu Harada, Joetsu (JP); Masaki Takeuchi, Joetsu (JP); Kazuo Shirota, Joetsu (JP); Kazuhiko Aoki, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 32 days.

(21) Appl. No.: 15/175,072

(22) Filed: Jun. 7, 2016

(65) Prior Publication Data

US 2016/0363856 A1 Dec. 15, 2016

(30) Foreign Application Priority Data

Jun. 10, 2015 (JP) ................. 2015-117442

(51) Int. Cl.
*G03F 1/60* (2012.01)
*B05D 1/28* (2006.01)
(Continued)

(52) U.S. Cl.
CPC ............ *G03F 1/60* (2013.01); *B05D 1/28* (2013.01); *C03C 17/32* (2013.01); *G01N 21/23* (2013.01); *G03F 1/20* (2013.01)

(58) Field of Classification Search
CPC .... G03F 1/60; G03F 1/20; B05D 1/28; G01N 21/23
See application file for complete search history.

(56) References Cited

U.S. PATENT DOCUMENTS

2007/0229795 A1* 10/2007 Zhang ............... G03F 7/2041
355/77
2010/0103420 A1* 4/2010 Pahl ............... G01M 11/0228
356/365
(Continued)

FOREIGN PATENT DOCUMENTS

EP 1 557 721 A2 7/2005
EP 2399708 A2 12/2011
(Continued)

OTHER PUBLICATIONS

Budhall, B. et al, "High Refractive Index Immersion Fluids for 193nm Immersion Lithoraphy", Opthomechatronic Micro/Nano Devices and Components III: Oct. 8-10, 2007, vol. 5754, pp. 622-629; cited in Extended European Search Report dated Feb. 8, 2017.
(Continued)

*Primary Examiner* — Elizabeth A Burkhart
(74) *Attorney, Agent, or Firm* — Westerman, Hattori, Daniels & Adrian, LLP (57) ABSTRACT

A synthetic quartz glass substrate is prepared by furnishing a synthetic quartz glass block, coating two opposite surfaces of the block with a liquid having a transmittance of at least 99.0%/mm at the wavelength of birefringence measurement, measuring a birefringence distribution on the block by letting light enter one coated surface and exit the other coated surface, and sorting the block to an acceptable group or unacceptable group, based on the measured birefringence distribution.

16 Claims, 2 Drawing Sheets

(51) Int. Cl.
 *C03C 17/32* (2006.01)
 *G01N 21/23* (2006.01)
 *G03F 1/20* (2012.01)

(56) References Cited

U.S. PATENT DOCUMENTS

| | | |
|---|---|---|
| 2011/0318995 A1 | 12/2011 | Okafuji et al. |
| 2013/0203324 A1* | 8/2013 | Hasegawa ................. B24B 1/00 451/41 |
| 2014/0120198 A1* | 5/2014 | Harada ................. B29C 59/022 425/385 |
| 2015/0360997 A1* | 12/2015 | Harada ................... C03C 17/00 427/8 |

FOREIGN PATENT DOCUMENTS

| | | |
|---|---|---|
| EP | 2 955 503 A1 | 12/2015 |
| JP | 63-154947 A | 6/1988 |
| JP | 8-75652 A | 3/1996 |
| JP | 2006-251781 A | 9/2006 |
| JP | 2006-273659 A | 10/2006 |
| JP | 2007-41312 A | 2/2007 |
| JP | 2011-26173 A | 2/2011 |
| JP | 2012-32786 A | 2/2012 |
| JP | 2013-140237 A | 7/2013 |
| JP | 2013-238849 A | 11/2013 |
| JP | 2015-112939 A | 6/2015 |
| JP | 2016-13964 A | 1/2016 |
| WO | 2006/085663 A1 | 8/2006 |
| WO | 2006/104179 A1 | 10/2006 |

OTHER PUBLICATIONS

Extended European Search Report dated Feb. 8, 2017, issued in counterpart European Application No. 16173733.3. (9 pages).
Office Action dated Feb. 27, 2018, issued in counterpart Japanese Application No. 2015-117442, with English machine translation. (11 pages).

* cited by examiner

METHOD FOR PREPARING SYNTHETIC QUARTZ GLASS SUBSTRATE

CROSS-REFERENCE TO RELATED APPLICATION

This non-provisional application claims priority under 35 U.S.C. § 119(a) on Patent Application No. 2015-117442 filed in Japan on Jun. 10, 2015, the entire contents of which are hereby incorporated by reference.

TECHNICAL FIELD

This invention relates to a method for preparing synthetic quartz glass substrates which are useful as nanoimprint lithography mask substrates for use in the fabrication of advanced semiconductor-related electronic materials, photomask substrates for use in the fabrication of liquid crystal panel displays, and photomasks for excimer laser lithography, typically ArF excimer laser lithography, especially ArF immersion lithography.

BACKGROUND ART

Higher levels of Integration in VLSI circuits have led to exposure patterns of increasingly small size. This has created a need for exposure light sources of shorter wavelength in the lithography systems or steppers used to write circuit patterns on semiconductor wafers. As a result, the mainstream light source in exposure tools has changed from the prior art KrF excimer laser (wavelength 248 nm) to ArF excimer laser (wavelength 193 nm). Recently the ArF immersion lithography is in practical application.

In the photolithography technology of the ArF immersion generation, it becomes the key to control the birefringence of photomask substrates. The photolithography technology adopts a system of transferring a photomask pattern to a resist film on a wafer by using ArF excimer laser as the light source, directing polarized illumination through a photomask substrate, and thus exposing the resist film pattern-wise. For transferring a pattern of finer feature size, it becomes important to improve the contrast. The contrast improvement is affected by such factors as flatness and birefringence of the photomask substrate. Birefringence manifests by residual strains or the like in quartz glass. If birefringence is significant, the polarization of light in the ArF immersion lithography tool is disturbed, leading to a decline of exposure performance.

For this reason, active research works are made how to control the birefringence of synthetic quartz glass substrates for photolithography. For example, Patent Document 1 discloses a mask blank for use in a semiconductor device fabrication technique employing an exposure light wavelength of 200 nm or shorter, comprising a synthetic quartz glass substrate and a light-shielding film laminated on the surface thereof, the mask blank having a birefringence value of 1 nm or less per substrate thickness at wavelength 193 nm. Patent Document 2 describes a process for producing a synthetic quartz glass having a birefringence value of 0.3 nm/cm or lower on the average at wavelength 633 nm. Patent Document 3 describes to heat treat synthetic quartz glass such that the major surface of a synthetic quartz glass block may have a maximum birefringence value of up to 2 nm/cm over its entirety.

Also, glass substrates used in the nanoimprint lithography (NIL) are required to have a high accuracy of shape or topography. The NIL is a technique of imprinting a nano-structured pattern to a resin for pattern transfer. The resolution of the pattern to be transferred depends on the resolution of nano-structures on the mold. Then the substrate on which a fine feature pattern is formed is required to have a high accuracy of shape. As mentioned above, birefringence manifests by residual strains or the like in quartz glass. If birefringence is significant, the substrate surface undergoes substantial changes of flatness and parallelism by the impact of residual stress, before and after processing synthetic quartz glass to a shape for NIL substrate. Such changes may lead to a focal shift during exposure and a pattern shift during transfer. To solve this problem, Patent Document 4 proposes a synthetic quartz glass substrate for microelectronic use having a maximum birefringence value of up to 3 nm/cm in its entirety.

Besides, the synthetic quartz glass members to be assembled in exposure tools and various other equipment used in the processes of manufacturing microelectronic and display components are also required to have a high purity and accuracy.

CITATION LIST

Patent Document 1: JP-A 2006-251781 WO 2006/085663)
Patent Document 2: JP-A 2006-273659 (WO 2006/104179)
Patent Document 3: JP-A 2011-026173
Patent Document 4: JP-A 2012-032786 (US 20110318995, EP 2399708)

SUMMARY OF INVENTION

In all of Patent Documents 1 to 4, a birefringence value is measured after a synthetic quartz glass substrate is polished to a mirror-like surface. This is based on the belief that birefringence is not measureable unless a glass substrate surface is light transmissive.

As mentioned above, the specifications required for photomask-forming synthetic quartz glass substrates and NIL glass substrates include flatness and flawlessness as well as birefringence. Even if the step of polishing a synthetic quartz glass substrate is modified so as to meet the flatness and defect specifications, the substrate is regarded rejected unless its birefringence value finally falls in the desired range. Although cumbersome costly steps are taken until a highly flat, flawless surface is reached, they run to waste, inviting a problem of low productivity.

An object of the invention is to provide a method for preparing synthetic quartz glass substrates having advantages including low birefringence, high flatness, and flawlessness, in a highly productive and economical manner, the substrates being useful as reticles and photomasks for use in excimer laser lithography, typically ArF excimer laser lithography, especially ArF immersion lithography, and NIL molds.

The Inventors have found that by coating a specific liquid to an arbitrary surface and an opposite surface of a synthetic quartz glass block or a synthetic quartz glass plate sliced therefrom, measuring a birefringence distribution on the block or plate by letting light enter one coated surface and exit the other coated surface, and sorting the block or plate to an acceptable or unacceptable group, on the basis of the measured birefringence distribution, it becomes possible to sort glass blocks or plates into acceptable and unacceptable groups in terms of one physical parameter, birefringence, at a relatively early stage of the synthetic quartz glass substrate manufacture process. Then synthetic quartz glass substrates can be prepared at a high productivity and low cost.

In one aspect, the invention provides a method for preparing a synthetic quartz glass substrate, comprising the steps of furnishing a synthetic quartz glass block, coating an arbitrary surface and an opposite surface of the block with a liquid, the liquid having a transmittance of at least 99.0%/mm at the wavelength of birefringence measurement, measuring a birefringence distribution on the block by letting light enter one coated surface and exit the other coated surface, and sorting the block to an acceptable group or unacceptable group, based on the measured birefringence distribution.

Preferably, in the sorting step, the block is sorted to the acceptable group when it has such a birefringence distribution that it has no maximum birefringence Inside an effective region on the block corresponding to an effective region on the resulting synthetic quartz glass substrate.

Preferably, in the sorting step, provided that the birefringence specification of synthetic quartz glass substrates is up to $\alpha$ nm/cm, the block is sorted to the acceptable group when it has a maximum birefringence value of up to $2.0\alpha$ nm/cm in a region corresponding to an effective region on the resulting synthetic quartz glass substrate.

Preferably, after the block is sorted to the acceptable group in the sorting step, the method further comprises the steps of slicing the block into a synthetic quartz glass plate, grinding or lapping, rough polishing, and final precise polishing the glass plate.

In another aspect, the invention provides a method for preparing a synthetic quartz glass substrate, comprising the steps of furnishing a synthetic quartz glass block, slicing the block into a synthetic quartz glass plate, coating an arbitrary surface and an opposite surface of the plate with a liquid, the liquid having a transmittance of at least 99.0%/mm at the wavelength of birefringence measurement, measuring a birefringence distribution on the plate by letting light enter one coated surface and exit the other coated surface, and sorting the plate to an acceptable group or unacceptable group, based on the measured birefringence distribution.

Preferably, in the sorting step, the plate is sorted to the acceptable group when it has such a birefringence distribution that it has no maximum birefringence inside an effective region on the plate corresponding to an effective region on the resulting synthetic quartz glass substrate.

Preferably, in the sorting step, provided that the birefringence specification of synthetic quartz glass substrates is up to $\alpha$ nm/cm, the plate is sorted to the acceptable group when it has a maximum birefringence value of up to $1.5\alpha$ nm/cm in a region corresponding to an effective region on the resulting synthetic quartz glass substrate.

Preferably, after the synthetic quartz glass plate is sorted to the acceptable group in the sorting step, the method further comprises the steps of grinding or lapping, rough polishing, and final precise polishing the glass plate.

In a preferred embodiment, the surface to be coated with the liquid has a roughness (Sa) of up to 1 mm.

In a preferred embodiment, the difference between the refractive index of the liquid and the refractive index of the synthetic quartz glass is within ±0.15.

The liquid is preferably selected from the group consisting of water, a monohydric alcohol, polyhydric alcohol, ether, aldehyde, ketone, carboxylic acid, hydrocarbon and an aqueous solution thereof. Most often the liquid is a polyhydric alcohol having a molecular weight of at least 200. Typically the liquid has a vapor pressure of lower than 3.2 kPa at 25° C. and 101.3 kPa.

ADVANTAGEOUS EFFECTS OF INVENTION

According to the invention, synthetic quartz glass substrates of appropriate grade for use as reticles and photomasks in excimer laser lithography, typically ArF excimer laser lithography, especially ArF immersion lithography, may be sorted out at a relatively early stage of the synthetic quartz glass substrate manufacture process, prior to any machining step, typically grinding step. The method for preparing synthetic quartz glass substrates is highly productive and economical.

DESCRIPTION OF PREFERRED EMBODIMENTS

Figure 1:
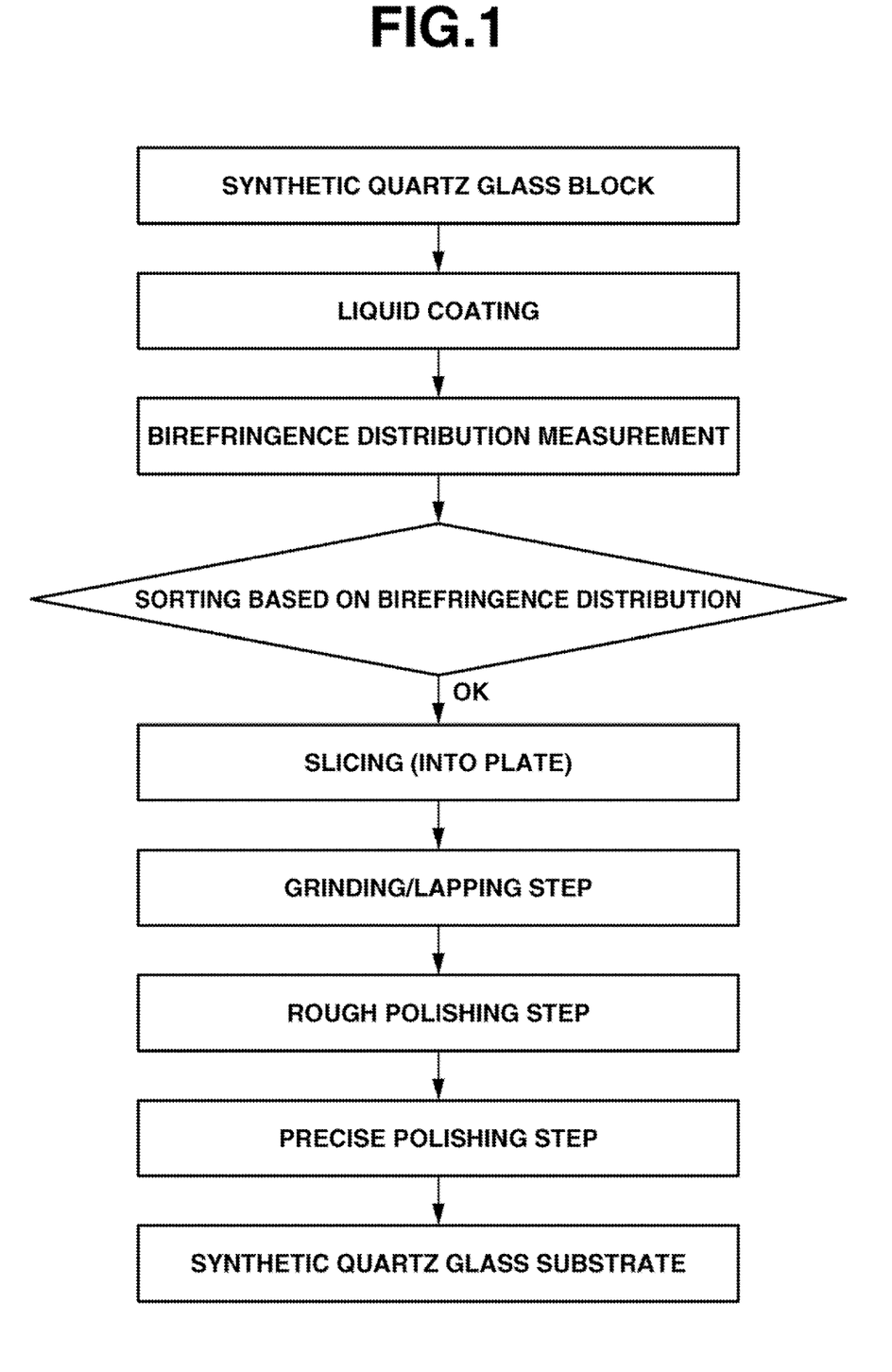
FIG. 1 is a flow diagram showing steps of synthetic quartz glass substrate preparation in one embodiment of the invention.

Referring to FIG. 1, the method for preparing synthetic quartz glass substrates according to the invention is described in detail. First, there is furnished a synthetic quartz glass block. It may be prepared by introducing a silica source compound such as a silane or siloxane compound into an oxyhydrogen flame, effecting vapor-phase hydrolysis or oxidative decomposition to form silica fine particles, depositing the particles on a target and vitrifying them, thus forming a synthetic quartz glass ingot. The ingot forming process may be either the direct process of depositing silica fine particles on the target and concurrently melting/vitrifying or the indirect process of depositing silica fine particles on the target and then heating for vitrification. The process is followed by placing the glass ingot in a high-purity carbon mold and holding it in a vacuum melting furnace at a temperature of 1,700 to 1,900° C. for 30 to 120 minutes, for thereby hot shaping the ingot into a block of desired shape. The synthetic quartz glass block may be of any shape such as tetragonal, rectangular or circular shape while it preferably has a diameter or longitudinal/transverse size of 150 to 300 mm and a thickness of 10 to 500 mm.

In one embodiment, a specific liquid is coated to two opposite surfaces of the synthetic quartz glass block for measuring a birefringence distribution on the block.

Figure 2:
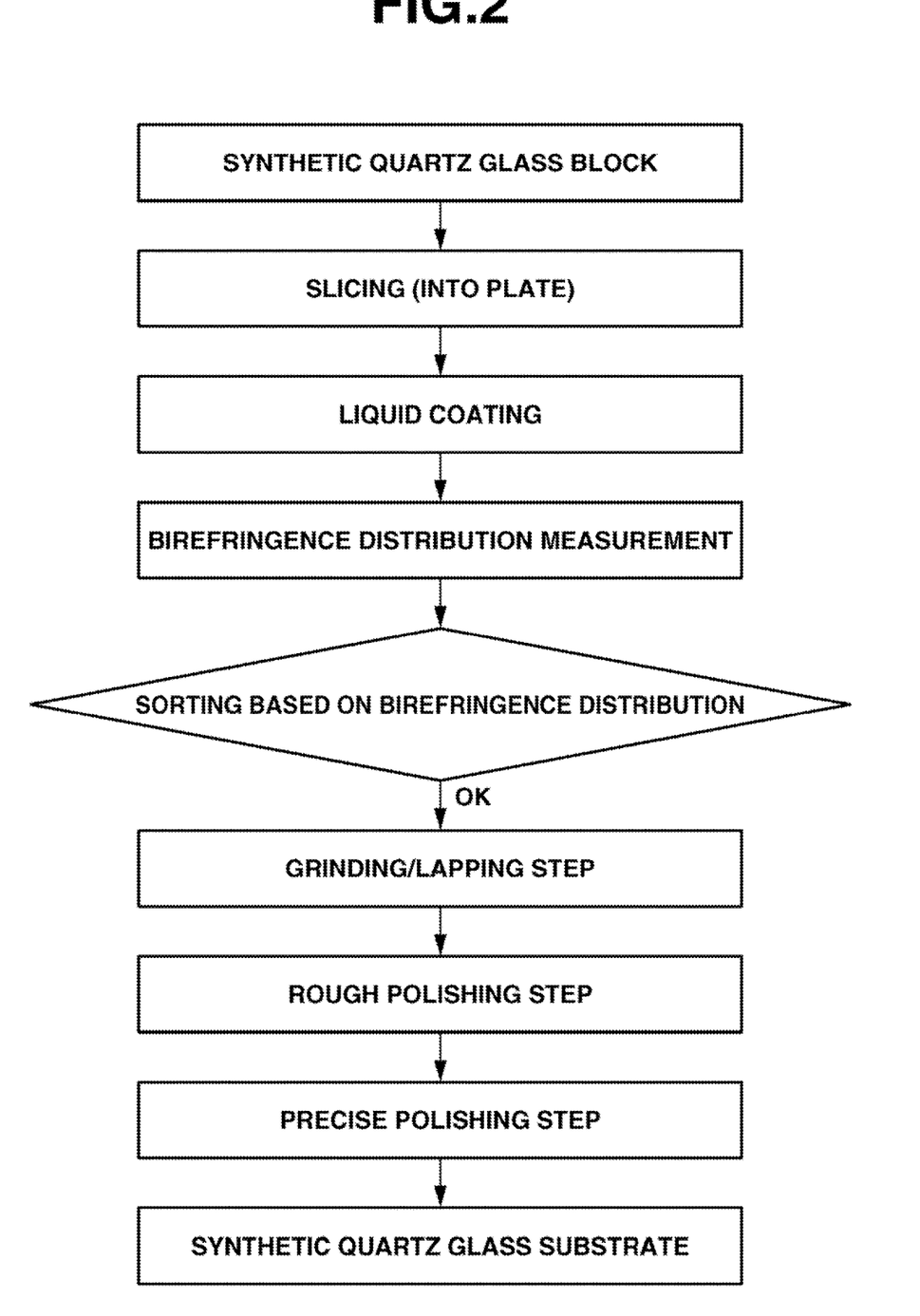
FIG. 2 is a flow diagram showing steps of synthetic quartz glass substrate preparation in another embodiment of the invention.

In another embodiment, as shown in FIG. 2, the synthetic quartz glass block is cut (or sliced) into plates by a slicing means or wire saw before the step of coating a specific liquid. As compared with the measurement of birefringence distribution at the block stage, the measurement of birefringence distribution on a glass plate provides for an accurate anticipation of the birefringence of a final product following lapping and mirror finishing. In this embodiment, the thickness of the glass plate depends on the thickness specification of the final product following lapping and mirror finishing. Preferably, the thickness of the glass plate is greater than the thickness of the final product by 10 μm to 1 mm, more preferably 50 μm to 500 μm. If the plate is too thick, an error from the birefringence of the final product may become noticeable, a greater machining allowance must be taken until processing to the final product, cumbersome work may be necessary, and a fraction of the material corresponding to the machining allowance may be wasted. If the plate is too thin, residual strains by cutting and lapping may be kept in the final product, which is rejected because of defects.

The method of the invention is advantageously applicable to the process of working and preparing 6-inch substrates [(152 mm±0.2 mm)×(152 mm±0.2 mm)×(6.35 mm±0.1 mm)] or 9-inch substrates [(228 mm±0.2 mm)×(228 mm±0.2 mm)×(6.35 mm±0.1 mm)]. The substrate is preferably made of synthetic quartz glass.

The liquid is coated to two surfaces of the synthetic quartz glass block or synthetic quartz glass plate, preferably rough surfaces which become light transmissive when coated with the liquid. The surface to be coated with the liquid preferably has a surface roughness (Sa) of up to 1 mm, more preferably 0.01 μm<Sa≤1 mm, even more preferably 0.1 μm<Sa≤100 μm, and most preferably 0.5 μm<Sa≤50 μm. A surface with Sa of less than 0.01 μm is nearly mirror-like and light transmissive as such, i.e., without liquid coating. If surface roughness Sa is more than 1 mm, surface irregularities are not fully buried even by coating of liquid, and then accurate birefringence distribution measurement may be inhibited by diffuse reflection of light at the incident and emergent surfaces.

The roughness of the surface to be coated with the liquid may be measured by means of a contact type instrument such as an atomic force microscope (AFM) or probe type roughness meter, or a non-contact type instrument such as a laser interferometer or white light interferometer. The range of measurement, in the case of measurement over two-dimensional plane, is preferably from 1 μm squares to 1 mm squares, more preferably from 10 μm squares to 100 μm squares, and in the case of measurement along one-dimensional length, is preferably from 10 μm to 10 mm, more preferably from 100 μm to 1 mm. If the measurement range is too narrow, an accurate roughness may not be determined. If the measurement range is too broad, measurement may be time consuming and become measurement of waviness or flatness, which is inadequate as the reference by which it is judged whether or not light transmission is increased by liquid coating.

The liquid coated to two opposite surfaces, an arbitrary surface and a surface opposed thereto of the synthetic quartz glass block or plate should have a transmittance of at least 99.0%/mm, preferably at least 99.5%/mm, and more preferably at least 99.9%/mm at the wavelength of light used in measurement of birefringence distribution. If the liquid has a transmittance of less than 99.0%/mm, which means that the liquid contains dyes or foreign matter as impurities, or if the liquid itself is absorptive, the birefringence distribution of a synthetic quartz glass block or plate cannot be accurately measured. This is because the quantity of light reaching the light-receiving sensor is reduced by scattering, or because the polarized state is disturbed upon passage through the liquid.

In general, the refractive index of a material varies with wavelength. There is a tendency that refractive index becomes higher as wavelength becomes shorter. Synthetic quartz glass has a refractive index of 1.457 to 1.561 in a wavelength range of 633 to 193 nm. It is preferred from the standpoint of acquisition of an accurate birefringence distribution that the difference between the refractive index of the liquid and the refractive index of synthetic quartz glass be in a range of ±0.15 (−0.15 to +0.15), more preferably ±0.10 (−0.10 to +0.10), and even more preferably ±0.05 (−0.05 to +0.05). That is, the refractive index of the liquid falls in a range of preferably RI±0.10, more preferably RI±0.10, and more preferably RI±0.05 wherein RI is the refractive index of synthetic quartz glass at the measurement wavelength.

The liquid to be coated may be selected from among water; monohydric alcohols of 1 to 12 carbon atoms; polyhydric alcohols such as ethylene glycol, diethylene glycol, triethylene glycol, propylene glycol, 1,3-butylene glycol, tetramethylene glycol, glycerol, polyethylene glycol, and phenol; ethers such as dimethyl ether, methyl ethyl ether, diethyl ether, tetrahydrofuran, 2,5-dimethylfuran, benzofuran, and dibenzofuran; aldehydes such as acetaldehyde, propionaldehyde and benzaldehyde; ketones such as acetone, methyl ethyl ketone, diethyl ketone and cyclohexanone; carboxylic acids of 1 to 8 carbon atoms such as saturated fatty acids, oleic acid, linoleic acid and linolenic acid; hydrocarbons of 5 to 17 carbon atoms such as linear alkanes; and aqueous solutions thereof. Since these liquids are relatively easy to handle and commercially available as reagents of guaranteed grade or purity, they are expected to be of consistent quality. Coating such liquid does not substantially affect birefringent properties of quartz glass, or if affects, the influence which is always constant can be previously taken into account. Of these, polyhydric alcohols having a molecular weight of at least 100, especially polyhydric alcohols having a molecular weight, specifically weight average molecular weight (Mw) of 200 to 2,000 as measured versus polystyrene standards by gel permeation chromatography (GPC) are preferred because they have an appropriate viscosity to coat to a rough glass surface and are readily washed away with water (i.e., ease of removal). Since polyhydric alcohols having a high molecular weight, typically polymers, tend to have a high viscosity, they, when coated onto a surface, are likely to remain on the surface. For instance, even when the glass surface where light is incident or emergent is placed downside, the surface maintains the coated state so that the birefringence distribution on a quartz glass block or plate may be consistently measured.

If the coated surface of the synthetic quartz glass block or plate becomes dry, light is not transmitted by the glass block or plate and an accurate birefringence distribution is not measurable. For the purpose of preventing the glass surface from drying, the liquid preferably has a vapor pressure of lower than 3.2 kPa, preferably lower than 1.4 kPa, at 25° C. and 101.3 kPa.

When the liquid is coated to two opposite surfaces, an arbitrary surface and an opposite surface of the synthetic quartz glass block or plate, any suitable means such as brush coating, spray coating, and spin coating may be used, Preferably from the standpoint of preventing the liquid from drying out so that an accurate birefringence distribution is not measurable, the coating step is conducted as quickly as possible and immediately followed by the step of measuring a birefringence distribution.

Next, the synthetic quartz glass block or plate having the two opposite surfaces coated with the liquid is measured for birefringence distribution by letting light enter one coated surface and exit the other coated surface. The birefringence distribution measurement may be performed by any suitable method. Since a high accuracy of measurement is desirable, the preferred systems are, for example, a birefringence measuring system ABR-10A (UNIOPT Co., Ltd.) composed of a common optical path interferometer of optical heterodyne method and a data processing/XY scan stage of Fourier analysis; Exicor series (HINDS Instruments) using photoelastic modulation in the optical system and including a plurality of lineups of 157 nm, 193 nm, and 633 nm as the light source; and birefringence evaluation system WPA-100

(Photonic Lattice, Inc.) comprising a light source section having a LED lamp combined with a circularly polarizing filter and a light receiving section having a polarizing filter integrated assembly combined with a CCD camera.

Specifically, on use of a measuring instrument using a laser light source like ABR-10A and Exicor, a laser spot has a small diameter of less than 1 mm, and a cross-sectional portion within the confine of the laser spot and in the optical path of laser beam in the glass may be determined for birefringence and major axis orientation on every measurement. When a birefringence value in an arbitrary range in glass is determined by such measuring instrument, for example, arbitrary measurement pitches are set in an arbitrary range (e.g., range of 140 mm×140 mm) on glass surface and inclusive of the end of the range, in both X and Y directions (e.g., X direction pitch 10 mm, Y direction pitch 10 mm) to determine points of measurement, and for each of data points of measurement (e.g., 225 points), birefringence value and major axis orientation are determined. From these data, data including maximum, minimum, average, and distribution of birefringence values and distribution of major axis orientation in an arbitrary range in the glass are acquirable.

On the other hand, on use of a measuring instrument of measuring birefringence values all at once in the LED illuminating area using a polarizing filter integrated assembly in the light receiving section, like WPA-100, depending on the distance between the CCD camera and the synthetic quartz glass and the resolution of the integrated assembly, measurement is made on the glass in the LED illuminating area. The glass surface is divided into arbitrary rectangular ranges (e.g., longitudinal/transverse 0.1 to 10 mm ranges) continuous in both X and Y directions, and the birefringence and major axis orientation of each finely divided area are determined. That is, the birefringence and major axis orientation in each area or cross section of the glass through which light passes may be determined. Among these, an arbitrary range to be evaluated is set, and each of the finely divided areas within that range is evaluated for birefringence and major axis orientation. Thus, data including maximum, minimum, average, and distribution of birefringence values and distribution of major axis orientation in the glass are acquirable.

This is followed by the step of sorting the synthetic quartz glass block or plate to an acceptable or unacceptable group. Based on the birefringence distribution obtained from the measurement by the above method, judgment is made from the maximum of birefringence values in a region on synthetic quartz glass block or plate corresponding to an effective region of the resulting synthetic quartz glass substrate. When the synthetic quartz glass block or plate has such a birefringence distribution that no maximum birefringence is inside a square region corresponding to an effective region on the resulting synthetic quartz glass substrate (that is, a maximum birefringence is outside the square region), there is a tendency that the birefringence value in a region corresponding to the effective region is affected by grinding the periphery of the block or plate such that the birefringence value inside the square region is reduced. This is presumably because the grinding operation affects residual stresses in the block to change the stress balance of the block.

Reference is now made to a synthetic quartz glass block of 187 mm×187 mm, for example. When the synthetic quartz glass block has such a birefringence distribution that no maximum birefringence appears inside a square region corresponding to an effective region (132 mm×132 mm) on the resulting synthetic quartz glass substrate (that is, a maximum birefringence appears outside the square region). provided that the birefringence specification of synthetic quartz glass substrates is a nm/cm (e.g., 2 nm/cm) or less, a synthetic quartz glass block having a maximum birefringence of 2.0α nm/cm (e.g., 4 nm/cm) or less in a region corresponding to an effective region (132 mm×132 mm) on the resulting synthetic quartz glass substrate (152 mm×152 mm) is sorted to the acceptable group. Then synthetic quartz glass substrates having a maximum birefringence value of up to 2 nm/cm are acquired in high yields.

On the other hand, when a synthetic quartz glass block has such a birefringence distribution that a maximum birefringence appears inside a region corresponding to an effective region (132 mm×132 mm) on the resulting synthetic quartz glass substrate, the birefringence value is not reduced even after grinding, and high birefringence sites are left, Thus the threshold value in the sorting step must be set at a nm/cm (e.g., 2 nm/cm) or less before synthetic quartz glass substrates having a maximum birefringence value of up to 2 nm/cm can be acquired in high yields.

It is provided that the birefringence specification of the synthetic quartz glass substrate is a nm/cm or less. Where the step of sorting a synthetic quartz glass block in terms of birefringence distribution is to sort a glass block to the acceptable group, the acceptable sorting (or judgment) is made when the maximum birefringence value in a region corresponding to an effective region on the resulting synthetic quartz glass substrate is preferably equal to or less than 2.0α nm/cm, more preferably equal to or less than 1.5α nm/cm, even more preferably equal to or less than 1.0α nm/cm. On the other hand, where the step of sorting a synthetic quartz glass plate in terms of birefringence distribution is to sort a glass plate to the acceptable group, the acceptable sorting (or judgment) is made when the maximum birefringence value in a region corresponding to an effective region on the resulting synthetic quartz glass substrate is preferably equal to or less than 1.5α nm/cm, more preferably equal to or less than 1.25α nm/cm, even more preferably equal to or less than 1.0α nm/cm.

Currently, synthetic quartz glass substrates having a maximum birefringence value of up to 2 nm/cm are required as the specifications of synthetic quartz glass substrates for photomasks of the ArF immersion lithography generation. A certain error occurs between the value of measurement of a synthetic quartz glass block or plate and the value of measurement of a synthetic quartz glass substrate which has been machined to a mirror-like surface. Thus if the threshold value of birefringence measured on the rough-surface block or plate is set low, there is a possibility that even those blocks or plates which provide a birefringence value of up to 2 nm/cm upon measurement of a synthetic quartz glass substrate obtained therefrom and machined to a mirror-like surface are judged unacceptable, indicating a possible waste of stock material. On the other hand, if the threshold value is set high, those out-of-specification substrates which exceed the birefringence value of 2 nm/cm upon measurement of a synthetic quartz glass substrate which has been machined to a mirror-like surface become more. Often an extra step of machining for flatness and flawlessness must be applied to such out-of-specification substrates, indicating poor productivity.

It has been described that on the assumption that the birefringence specification is a nm/cm (e.g., 2 nm/cm), sorting of a synthetic quartz glass block after the birefringence measurement is based on the maximum birefringence value of 2.0α nm/cm (e.g., 4 nm/cm), whereas a synthetic quartz glass substrate which has been machined to a mirror-like surface is judged acceptable or unacceptable using the birefringence value of 2 nm/cm as the threshold. A difference is introduced between the threshold values by taking an error into account because it is difficult to accurately anticipate the birefringence value of a synthetic quartz glass substrate (sliced from a block) from the birefringence distribution of a synthetic quartz glass block. The block is thick as compared with the substrate. Thus, if the birefringence value varies in thickness direction, the measured birefringence value of the block is substantially the average of values in thickness direction. That is, a variation in birefringence value may occur among synthetic quartz glass substrates sliced from the block. At the stage of block, the birefringence distribution of a block in a region assumed to be commensurate with the effective region on a substrate is measured. When a birefringence value of a substrate is anticipated from this measurement, an error of several millimeters may sometimes be introduced. There are further variable factors, for example, coating of the liquid is uneven, and a slight error is introduced even when the liquid is selected so that the difference in refractive index between the liquid and the quartz glass is within ±0.15. Because of these factors, it is difficult to accurately anticipate the birefringence value of a glass substrate (sliced from the block) from the measured birefringence distribution of a glass block.

For the above reason, if the stock material is precious or if its cost is relatively high, preferably the threshold for sorting blocks is set slightly higher than the threshold for judging whether the synthetic quartz glass substrate which has been polished to a mirror-like surface is acceptable or unacceptable. On the other hand, if the stock material is relatively easy to prepare or if its cost is relatively low and the cost of machining steps is relatively high (for example, specifications regarding flatness and defectiveness are high), the flow chart may be, designed such that the birefringence threshold for sorting blocks is set severer than the threshold for judging whether the birefringence value of synthetic quartz glass substrate is acceptable or unacceptable. Such setting increases the percent pass rate of final substrates in terms of birefringence specification and minimizes the cost of machining steps.

On the other hand, when the birefringence specification required for products is moderate, the threshold may be set high. In this case, the threshold for sorting blocks is set low with a tolerance so that substantially all substrates are judged acceptable, while an error between the birefringence measurement of a synthetic quartz glass block and the birefringence measurement of a substrate due to variations among substrates is taken into account. Yet satisfactory yields are obtained. In such case, it may be contemplated to judge blocks to be acceptable or not, based on the measurement values of blocks rather than the cumbersome step of measuring all substrates. This process is economical due to the reduced number of measurements.

After the sorting step, in the case of a synthetic quartz glass block, which is judged acceptable, the liquid which has been coated to the block for measurement of birefringence distribution is removed, and the block is cut or sliced into plates. In the case of a synthetic quartz glass plate, the liquid is similarly removed after the sorting step. In either case, the plate is then subjected to grinding or lapping, rough polishing and precise polishing steps, yielding a synthetic quartz glass substrate. These polishing steps may be carried out by standard techniques used in the prior art. Finally, there are produced synthetic quartz glass substrates typically having a surface roughness Ra of 0.05 to 1 nm and a birefringence value of up to 2 nm/cm.

According to the invention, synthetic quartz glass blocks or plates are sorted in terms of birefringence distribution at the relatively early stage of the process of machining and preparing synthetic quartz glass substrates. Then several advantages are expectable in the manufacture of synthetic quartz glass substrates for forming reticles and photomasks for use in the ArF excimer laser lithography, and especially ArF immersion lithography. When (1) substrates having a birefringence value of 2 nm/cm, a flatness of 0.3 µm, and required to have a surface free of defects or foreign particles in excess of 0.1 µm (for example, synthetic quartz glass substrates suited for a particular grade of photomask-forming synthetic quartz glass substrates, that is, photomask-forming synthetic quartz glass substrates subject to severe specifications requiring high-level physical properties), and (2) substrates having an arbitrary birefringence value, a flatness of 0.8 µm, and required to have a surface free of defects or foreign particles in excess of 1.0 µm (for example, photomask-forming synthetic quartz glass substrates subject to relatively moderate specifications) are prepared in a separate manner, sorting in terms of birefringence distribution is carried out at the stage of stock material which is processed via later steps including grinding or lapping step, rough polishing step, and final precision polishing step into a precisely mirror-finished glass substrate, that is, at the stage of a synthetic quartz glass block or a synthetic quartz glass plate sliced therefrom. Then, only those stock materials which are anticipated to fall in the specification: birefringence value of 2 nm/cm are processed so as to meet flatness and defect specifications whereas excessive processing of those stock materials which are anticipated not to fall in the specification is avoidable. As a result, photomask-forming synthetic quartz glass substrates can be prepared in a highly productive and economic manner.

EXAMPLE

Examples are given below by way of illustration and not by way of limitation.

Example 1

There was furnished a synthetic quartz glass block of 187 mm long×187 mm wide×50 mm thick and having a surface roughness (Sa) of 2.0 µm. Two opposite (187 mm×187 mm) surfaces of the block were evenly brush coated with polyethylene glycol (PEG, Polyethylene Glycol 400 by Wako Pure Chemical Industries, Ltd.) so that light might enter one coated surface and exit the other coated surface. Using birefringence evaluation system WPA-100 (Photonic Lattice, Inc.), a birefringence distribution on the PEG-coated surface at wavelength 543 nm was measured at room temperature (25° C.). In the birefringence distribution of the block, the maximum birefringence appeared outside a square region of 152 mm 152 mm, that is, no maximum birefringence appeared in an effective region on the block corresponding to an effective region (132 mm×132 mm squares) on a 6-inch substrate (152 mm×152 mm squares) sliced therefrom in a later step. It is noted that the birefringence value of the block is converted to a birefringence value at wavelength 193 nm by multiplying a maximum value in the square region of 132 mm×132 mm by 1.48. The maximum of birefringence values of the block after conversion was 4.1 nm/cm. The synthetic quartz glass block was sorted to be processed for the manufacture of substrates of the grade meeting birefringence 2 nm/cm specification.

Thereafter, the block was sliced into plates. Each plate was subjected to lapping step, rough polishing step on a double-side polishing machine using a hard urethane polishing pad and cerium oxide abrasive slurry, and final precision polishing on a double-side polishing machine using a suede polishing pad and colloidal silica abrasive slurry. There were obtained six synthetic quartz glass substrates of 6 inch squares and 6.35 mm thick having a precision mirror-like surface.

Each of the synthetic quartz glass substrates was measured for birefringence value in an effective region 132 mm×132 mm squares). As a result, the maximum birefringence at wavelength 193 nm was 1.3, 1.7, 1.5, 1.8, 1.8 and 2.6 nm/cm, indicating that five of six substrates were acquired as the 2 nm/cm specification grade.

Example 2

There was furnished a synthetic quartz glass block of 187 mm long×187 mm wide×50 mm thick and having a surface roughness (Sa) of 2.0 μm. Two opposite (187 mm×187 mm) surfaces of the block were evenly brush coated with PEG so that light might enter one coated surface and exit the other coated surface. A birefringence distribution on the PEG-coated surface at wavelength 543 nm was measured at room temperature (25° C.). In the birefringence distribution of the block, a maximum birefringence appeared outside a square region of 152 mm×152 mm, that is, no maximum birefringence appeared in an effective region on the block corresponding to an effective region (132 mm×132 mm squares) on a 6-inch substrate (152 mm×152 mm squares) sliced therefrom in a later step. It is noted that the birefringence value of the block is converted to a birefringence value at wavelength 193 nm by multiplying a maximum value in the square region of 132 mm×132 mm by 1.48. The maximum of birefringence values of the block after conversion was 2.3 nm/cm. The synthetic quartz glass block was sorted to be processed for the manufacture of substrates of the grade meeting birefringence 2 nm/cm specification.

Thereafter, the block was sliced into plates. Each plate was subjected to lapping step, rough polishing step on a double-side polishing machine using a hard urethane polishing pad and cerium oxide abrasive slurry, and final precision polishing on a double-side polishing machine using a suede polishing pad and colloidal silica abrasive slurry. There were obtained six synthetic quartz glass substrates of 6 inch squares and 6.35 mm thick having a precision mirror-like surface.

Each of the synthetic quartz glass substrates was measured for birefringence value in an effective region (132 mm×132 mm squares). As a result, the maximum birefringence at wavelength 193 nm was 1.0, 0.9, 1.2, 1.4, 1.4 and 1.2 nm/cm, indicating that six of six substrates were acquired as the 2 nm/cm specification grade (yield 100%).

Example 3

There was furnished a synthetic quartz glass block of 260 mm long×260 mm wide×50 mm thick and having a surface roughness (Sa) of 2.0 μm. Two opposite (260 mm×260 mm) surfaces of the block were evenly brush coated with PEG so that light might enter one coated surface and exit the other coated surface. A birefringence distribution on the PEG coated surface at wavelength 543 nm was measured at room temperature (25° C.). In the birefringence distribution of the block, a maximum birefringence appeared outside a square region of 228 mm×228 mm, that is, no maximum birefringence appeared in an effective region on the block corresponding to an effective region (208 mm×208 mm squares) on a 9-inch substrate (228 mm×228 mm squares) sliced therefrom in a later step. It is noted that the birefringence value of the block is converted to a birefringence value at wavelength 193 nm by multiplying a maximum value in the square region of 208 mm×208 mm by 1.48. The maximum of birefringence values of the block after conversion was 2.4 nm/cm. The synthetic quartz glass block was sorted to be processed for the manufacture of substrates of the grade meeting birefringence 2 nm/cm specification.

Thereafter, the block was sliced into plates. Each plate was subjected to lapping step, rough polishing step on a double-side polishing machine using a hard urethane polishing pad and cerium oxide abrasive slurry, and final precision polishing on a double-side polishing machine using a suede polishing pad and colloidal silica abrasive slurry. There were obtained six synthetic quartz glass substrates of 9 inch squares and 6.35 mm thick having a precision mirror-like surface.

Each of the synthetic quartz glass substrates was measured for birefringence value in an effective region (208 mm×208 mm squares). As a result, the maximum birefringence at wavelength 193 nm was 1.9, 1.6, 1.5, 1.7, 1.8 and 1.2 nm/cm, indicating that six of six substrates were acquired as the 2 nm/cm specification grade (yield 100%).

Example 4

There was furnished a synthetic quartz glass plate of 152 mm long×152 mm wide×6.90 mm thick and having a surface roughness (Sa) of 1.5 μm. Two opposite (152 mm×152 mm) surfaces of the plate were evenly brush coated with PEG so that light might enter one coated surface and exit the other coated surface. A birefringence distribution on the PEG-coated surface at wavelength 543 nm was measured at room temperature (25° C.). In the birefringence distribution of the plate, a maximum birefringence appeared outside a square region of 140 mm×140 mm, that is, no maximum birefringence appeared in an effective region on the plate corresponding to an effective region (132 mm×132 mm squares) on a 6-inch substrate (152 mm×152 mm squares) obtained therefrom in a later step. It is noted that the birefringence value of the plate is converted to a birefringence value at wavelength 193 nm by multiplying a maximum value in the range of 132 mm×132 mm squares by 1.48. The maximum of birefringence values of the block after conversion was 4.8 nm/cm. The synthetic quartz glass plate was sorted to be processed for the manufacture of substrates of the grade meeting birefringence 5 nm/cm specification.

Thereafter, the plate was subjected to lapping step, rough polishing step on a double-side polishing machine using a hard urethane polishing pad and cerium oxide abrasive slurry, and final precision polishing on a double-side polishing machine using a suede polishing pad and colloidal silica abrasive slurry. There was obtained a synthetic quartz glass substrate of 6 inch squares and 6.35 mm thick having a precision mirror-like surface.

The synthetic quartz glass substrate was measured for birefringence value in an effective region (132 mm×132 mm squares). As a result, the maximum birefringence at wavelength 193 nm was 4.7 nm/cm, indicating that the substrate met the 5 nm/cm specification grade.

Example 5 (Sorted to Unacceptable Group)

There was furnished a synthetic quartz glass block of 187 mm long×187 mm wide×50 mm thick and having a surface roughness (Sa) of 2.0 µm. Two opposite (187 mm×187 mm) surfaces of the block were evenly brush coated with PEG so that light might enter one coated surface and exit the other coated surface. A birefringence distribution on the PEG-coated surface at wavelength 543 nm was measured at room temperature (25° C.). In the birefringence distribution of the block, a maximum birefringence appeared inside an effective region on the block corresponding to an effective region (132 mm×132 mm squares) on a 6-inch substrate (152 mm×152 mm squares) sliced therefrom in a later step. It is noted that the birefringence value of the block is converted to a birefringence value at wavelength 193 nm by multiplying a maximum value in the square region of 132 mm×132 mm by 1.48. The maximum of birefringence values of the block after conversion was 3.2 nm/cm.

Thereafter, the block was sliced into plates. Each plate was subjected to lapping step, rough polishing step on a double-side polishing machine using a hard urethane polishing pad and cerium oxide abrasive slurry, and final precision polishing on a double-side polishing machine using a suede polishing pad and colloidal silica abrasive slurry. There were obtained six synthetic quartz glass substrates of 6 inch squares and 6.35 mm thick having a precision mirror-like surface.

Each of the synthetic quartz glass substrates was measured for birefringence value in an effective region (132 mm×132 mm squares). As a result, the maximum birefringence at wavelength 193 nm was 2.9, 3.5, 3.3, 2.7, 3.3 and 2.8 nm/cm, indicating that none of six substrates were acquired as the 2 nm/cm specification grade. If sorting at the stage of rough-surface synthetic quartz glass block was omitted and the block was used for the manufacture of substrates of the 2 nm/cm specification grade, no substrates of the desired grade would be acquired, that is, waste substrates would be manufactured.

Example 6 (Sorted to Unacceptable Group)

There was furnished a synthetic quartz glass plate of 152 mm long×152 mm wide×6.90 mm thick and having a surface roughness (Sa) of 1.5 µm. Two opposite (152 mm×152 mm) surfaces of the plate were evenly brush coated with PEG so that light might enter one coated surface and exit the other coated surface. A birefringence distribution on the PEG-coated surface at wavelength 543 nm was measured at room temperature (25° C.). In the birefringence distribution of the plate, a maximum birefringence appeared inside an effective region on the plate corresponding to an effective region (132 mm×132 mm squares) on a 6-inch substrate (152 mm×152 mm squares) obtained therefrom in a later step. It is noted that the birefringence value of the block is converted to a birefringence value at wavelength 193 nm by multiplying a maximum value in the square region of 132 mm×132 mm by 1.48. The maximum of birefringence values of the plate after conversion was 2.6 nm/cm.

Thereafter, the plate was subjected to lapping step, rough polishing step on a double-side polishing machine using a hard urethane polishing pad and cerium oxide abrasive slurry, and final precision polishing on a double-side polishing machine using a suede polishing pad and colloidal silica abrasive slurry. There was obtained a synthetic quartz glass substrate of 6 inch squares and 6.35 mm thick having a precision mirror-like surface.

The synthetic quartz glass substrate was measured for birefringence value in an effective region (132 mm×132 mm squares). As a result, the maximum birefringence at wavelength 193 nm was 2.5 nm/cm, indicating that the substrate was not acquired as the 2 nm/cm specification grade. If sorting at the stage of rough-surface synthetic quartz glass plate was omitted and the plate was used for the manufacture of substrates of the 2 nm/cm specification grade, no substrates of the desired grade would be acquired, that is, waste substrates would be manufactured.

Japanese Patent Application No. 2015-117442 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing a synthetic quartz glass substrate for a nanoimprint lithography mask substrate or photomask substrate, comprising the steps of:
   furnishing a synthetic quartz glass block,
   coating the block with a liquid at two surfaces consisting of a first surface and a second surface-opposite to the first surface, the liquid having a transmittance of at least 99.0%/mm at the wavelength of birefringence measurement,
   measuring a birefringence distribution on the block including a maximum birefringence by letting light enter the block through the liquid coated on the first surface and exit the block through the liquid coated on the second surface, and
   sorting the block to an acceptable group or unacceptable group, based on the measured birefringence distribution,
   wherein in the sorting step, the block is sorted to the acceptable group when it has such a birefringence distribution that the maximum birefringence is outside an effective region on the block corresponding to an effective region on the resulting synthetic quartz glass substrate.

2. The method of claim 1 wherein in the sorting step, provided that the birefringence specification of synthetic quartz glass substrates is up to α nm/cm, the block is sorted to the acceptable group when it has a maximum birefringence value of up to 2.0α nm/cm in a region corresponding to an effective region on the resulting synthetic quartz glass substrate.

3. The method of claim 1 wherein after the block is sorted to the acceptable group in the sorting step, said method further comprises the steps of slicing the block into a synthetic quartz glass plate, grinding or lapping, rough polishing, and final precise polishing the glass plate.

4. The method of claim 1 wherein the first surface and the second surface to be coated with the liquid has a roughness (Sa) of up to 1 mm.

5. The method of claim 1 wherein the difference between the refractive index of the liquid and the refractive index of the synthetic quartz glass is within ±0.15.

6. The method of claim 1 wherein the liquid is selected from the group consisting of water, a monohydric alcohol, polyhydric alcohol, ether, aldehyde, ketone, carboxylic acid, hydrocarbon and an aqueous solution thereof.

7. The method of claim 1 wherein the liquid is a polyhydric alcohol having a molecular weight of at least 200.

8. The method of claim 1 wherein the liquid has a vapor pressure of lower than 3.2 kPa at 25° C. and 101.3 kPa.

9. A method for preparing a synthetic quartz glass substrate for a nanoimprint lithography mask substrate or photomask substrate, comprising the steps of:
furnishing a synthetic quartz glass block,
slicing the block into a synthetic quartz glass plate,
coating the plate with a liquid at two surfaces consisting of a first surface and a second surface opposite to the first surface, the liquid having a transmittance of at least 99.0%/mm at the wavelength of birefringence measurement,
measuring a birefringence distribution on the plate including a maximum birefringence by letting light enter the block through the liquid coated on the first surface and exit the block through the liquid coated on the second surface, and
sorting the plate to an acceptable group or unacceptable group, based on the measured birefringence distribution,
wherein in the sorting step, the plate is sorted to the acceptable group when it has such a birefringence distribution that the maximum birefringence is outside an effective region on the plate corresponding to an effective region on the resulting synthetic quartz glass substrate.

10. The method of claim 1, wherein the synthetic quartz glass block has a tetragonal shape.

11. The method of claim 1, wherein in the sorting step, the block is acceptable if it has maximum of birefringence outside the effective region.

12. The method of claim 1 or 9, wherein the liquid is coated by brush coating, spray coating, or spin coating.

13. The method of claim 9 wherein in the sorting step, provided that the birefringence specification of synthetic quartz glass substrates is up to a nm/cm, the plate is sorted to the acceptable group when it has a maximum birefringence value of up to 1.5α nm/cm in a region corresponding to an effective region on the resulting synthetic quartz glass substrate.

14. The method of claim 9 wherein after the synthetic quartz glass plate is sorted to the acceptable group in the sorting step, said method further comprises the steps of grinding or lapping, rough polishing, and final precise polishing the glass plate.

15. The method of claim 9, wherein the synthetic quartz glass plate has a tetragonal shape.

16. The method of claim 9, wherein in the sorting step, the plate is acceptable if it has maximum of birefringence outside the effective region.

* * * * *